United States Patent [19]

Stapp

[11] 4,026,924
[45] May 31, 1977

[54] PROCESS OF PREPARING DIACYLOXY OLEFINS

[75] Inventor: Paul R. Stapp, Bartlesville, Okla.

[73] Assignee: Phillips Petroleum Company, Bartlesville, Okla.

[22] Filed: Apr. 10, 1975

[21] Appl. No.: 566,753

[52] U.S. Cl. .......................... 260/497 R; 260/410; 260/410.5; 260/410.6; 260/465 D; 260/465.4; 260/468 R; 260/468 K; 260/475 N; 260/476 R; 260/485 L; 260/485 N; 260/487

[51] Int. Cl.² ........................................ C07C 67/05

[58] Field of Search ............ 260/497 R, 410.6, 410, 260/410.5, 465 D, 465.4, 468, 475 N, 476, 485, 487

[56] References Cited

UNITED STATES PATENTS

| | | | |
|---|---|---|---|
| 2,316,604 | 4/1943 | Loder | 260/497 R |
| 3,689,535 | 9/1972 | Kollar | 260/497 R |
| 3,723,510 | 3/1973 | Ono | 260/497 R |

*Primary Examiner*—Lorraine A. Weinberger
*Assistant Examiner*—Michael Shipper

[57] ABSTRACT

Diacyloxy olefins are prepared by the reaction of a conjugated diolefin with a carboxylic acid in the presence of free oxygen and a catalyst system consisting essentially of an alkali metal compound and a compound of gold or silver.

10 Claims, No Drawings

PROCESS OF PREPARING DIACYLOXY OLEFINS

This invention relates to a process for the production of unsaturated diesters.

Various methods for the production of unsaturated diesters are known in the art.

It is an object of this invention to provide a novel process for the production of unsaturated diesters.

Other objects, aspects and advantages of this invention will be readily apparent to those skilled in the art from the reading of the following disclosure.

In accordance with the present invention there is provided a process for the production of unsaturated diesters which comprises reacting a conjugated diolefin with a carboxylic acid in the presence of free oxygen and a catalyst system consisting essentially of an alkali metal compound and a compound of a metal selected from the group consisting of gold and silver.

The conjugated diolefin is selected from the group consisting of acyclic conjugated diolefins having from 4 to 16 carbon atoms per molecule and corresponding to the general formula

and cyclic conjugated diolefins having from 5 to 16 carbon atoms per molecule and corresponding to the general formula

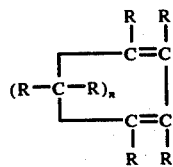

wherein, in each of the above formulas, R can be hydrogen, halogen, cyano, —COOR' or a hydrocarbyl radical containing up to 12 carbon atoms selected from the group consisting of alkyl, aryl, cycloalkyl and combinations thereof, such as aralkyl, alkaryl and the like. R' can be hydrogen, alkyl radical of up to 10 carbon atoms or aryl radical of up to 10 carbon atoms. The integer n can range from 1 to 12.

Examples of suitable conjugated diolefins include: 1,3-butadiene, 2-methyl-1,3-butadiene, 2-chloro-1,3-butadiene, 2-ethyl-1,3-butadiene, 2-chloro-3-methyl-1,3-butadiene, 1,4-diphenyl-1,3-butadiene, 1,3-hexadiene, 1,3-pentadiene, 1,3-octadiene, 1,3-cyclohexadiene, 1,3-cyclooctadiene, 1,3-cyclododecadiene, 2-cyano-1,3-butadiene, 5-methyl-1,3-cyclohexadiene, 2,4-cyclohexadiene-1,2-dicarboxylic acid, octafluoro-1,3-cyclohexadiene, hexachloropentadiene, 5,6,7,8-tetrabromo-1,3-cyclooctadiene, 2-cyclohexyl-1,3-butadiene, 2-methylene-3-butenoic acid, 2,4-pentadienenitrile, cyclopentadiene, 2-carbethoxy-1,3-butadiene, and the like.

In a presently preferred embodiment the conjugated diolefins employed in the process of this invention are those which contain only carbon and hydrogen.

In a more preferred embodiment the conjugated diolefin is acyclic diolefin wherein R, in the above formula, is hydrogen or alkyl of up to 12 carbon atoms.

The carboxylic acid is selected from the group consisting of monocarboxylic acids having from 2 to 18 carbon atoms per molecule characterized by the general formula

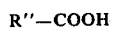

and dicarboxylic acids having from 2 to 18 carbon atoms per molecule characterized by the formula

wherein R" is selected from the group consisting of alkyl, cycloalkyl and aryl radicals and halogen, cyano and —COOR' substituted derivatives thereof, wherein up to four halogen, cyano or —COOR' substituents can be present in the R" group; and wherein R''' is selected from the group consisting of a valence bond and alkylene, cycloalkylene and arylene radicals and halogen, cyano and —COOR' substituted derivatives thereof, wherein up to four halogen, cyano or —COOR' substituents can be present in the R''' group. R' has been previously defined.

In a presently preferred embodiment, the carboxylic acid is a monocarboxylic acid.

Examples of suitable carboxylic acids include: acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, oxalic acid, succinic acid, adipic acid, terephthalic acid, 2-bromobutanoic acid, ethyl hydrogen adipate, 4-chlorobenzoic acid, 4-cyanobenzoic acid, 2,3,4,5-tetrachlorobenzoic acid, ethyl hydrogen-o-phthalate, and the like.

The reaction according to this invention is carried out by the catalytic action of a catalyst system consisting essentially of a compound of gold or silver together with an alkali metal compound. Suitable compounds of gold and/or silver include the halides, carboxylates, oxides, sulfates and mixtures thereof.

Examples of suitable compounds of silver or gold include Ag(I) acetate, AgBr, AgCl, $Ag_2CO_3$, Ag(I) citrate, Ag(I) laurate, Ag(I) oxalate, $Ag_2O$, $Ag_2SO_4$, AuBr, $AuBr_3$, AuCl, $AuCl_3$, $Au_2O_3$, $Au_2S$, $Au_2S_3$ and the like.

Further, one or more of the suitable compounds of gold or silver can be dispersed in or upon an inert support material, such as silica, alumina, silica-alumina, clay and the like.

The second component of the catalyst system is an alkali metal compound such as a halide, carboxylate or oxide. Of the alkali metal compounds, the lithium compounds are especially preferred.

Examples of suitable alkali metal compounds which can be employed as catalyst components include: lithium chloride, lithium bromide, lithium iodide, lithium acetate, lithium benzoate, lithium oxide, lithium octadecanoate, sodium chloride, sodium bromide, sodium acetate, potassium chloride, potassium acetate, potassium benzoate, rubidium chloride, rubidium bromide, rubidium acetate, cesium chloride, cesium acetate, cesium oxide and the like and mixtures thereof.

The gold or silver compound is employed in an amount ranging from about 0.1 to about 25 mole percent, based on the conjugated diene. It is presently preferred that the gold/silver compound be present in an amount ranging from about 5 to about 20 mole percent.

The alkali metal compound is employed in an approximate amount ranging from 0.1 to 2 molar, based upon the carboxylic acid present as diluent and reactant. It is presently preferred that the alkali metal compound be employed in an approximate amount ranging from 0.7 to 1.5 molar.

The reaction of the instant invention is an oxidation reaction and as such is carried out in the presence of free oxygen. The amount of oxygen present is not believed to be critical though it is recognized that an undesirably slow reaction will result if the concentration of oxygen is very low. Essentially pure oxygen can be employed as well as mixtures of oxygen with inert gases or air can be employed as a source of free oxygen for the instant reaction. It is recognized that explosive conditions could be obtained if the amount of oxygen added to the reaction system is not under control. The reaction of this invention, as is true with many oxidation reactions, appears to be highly exothermic and this too indicates caution in adding oxygen to the system. Because of these considerations it is desirable to add the oxygen incrementally or continuously during the reaction to avoid the explosive range of oxygen concentration and to allow better control of the temperature of the reaction. A reaction vessel with efficient mixing means is also desirable to avoid build-up of dangerous concentrations of free oxygen.

The reaction of this invention is carried out at a temperature in the range of 30° to about 200° C, preferably from about 100° to about 150° C.

The reaction is carried out at a pressure of from 0.1 to 1000, preferably from 5 to 200 psig, of oxygen above autogenous pressure at the temperature employed.

The reaction time is not critical and can range from 0.1 to about 12 hours. The reaction time depends upon the temperature, catalyst activity and the oxygen pressure employed.

As described above, the reaction of the instant invention is carried out in the presence of a carboxylic acid which provides the acyl moiety of the final product. It is optional, though presently preferred, to employ, as part of the reaction mixture, the corresponding carboxylic acid anhydride in addition to the carboxylic acid. The use of a carboxylic anhydride serves to simplify the purification and separation steps by reducing the amount of by-products which contain free hydroxy groups.

The process of this invention can be carried out in a batch or a continuous fashion.

The process of this invention can be carried out in the liquid phase or in the gas phase.

In a presently preferred embodiment of this invention, the process of this invention is carried out in the liquid phase.

When conducted in the liquid phase, it is preferred that the carboxylic acid employed in the process of this invention be normally liquid or at least liquid under the conditions employed for the reaction. The presently preferred carboxylic acid is acetic acid.

When carried out in the liquid phase, the carboxylic acid serves as the reaction medium. It is within the scope of this invention to utilize a hydrocarbon diluent as the reaction medium. Such diluent must be resistant to oxidation in the reaction described above. Suitable diluents include benzene, toluene, cyclohexane, saturated aliphatic hydrocarbons and the like. When a diluent is used, the carboxylic acid must be present in an amount sufficient to provide at least two moles of carboxylic acid per mole of conjugated diene.

It is also within the scope of this invention to use less than a stoichiometric quantity of the dicarboxylic acid to produce polyesters.

Reaction mixtures obtained according to the process of this invention are generally vented to remove any unreacted oxygen and conjugated diolefin and then distilled to remove the carboxylic acid and anhydride, if present. The product remaining is usually distilled to recover one or more fractions containing the diacyloxy olefins. The catalyst can be recovered from the distillation residue and recycled to the reaction zone as desired. Any unreacted conjugated diolefin recovered from the reaction mixture can also be recycled to the reaction zone as desired. The diacloxy olefins which are recovered from the product mixture include in many instances an amount of 1,2- or vicinal- isomer which can be recycled to the reaction zone and thereby converted to the desired 1,4-diacyloxy olefin.

The above mentioned 1,4-diacyloxy olefins have utility as intermediates for the preparation of the corresponding saturated diols. The 1,4-diacyloxy olefins are also useful intermediates in the preparation of tetrahydrofurans. For example, British Pat. No. 1,170,222 describes the ultimate preparation of tetrahydrofurans starting with conjugated diolefins and proceeding through the 1,4-diacyloxy butenes. Tetrahydrofuran itself, of course, would be produced starting with 1,3-butadiene. The above described esters are also useful as plasticizers for thermoplastic resins.

The following examples illustrate the invention.

EXAMPLE 1

A run was conducted according to the instant invention employing a 250 ml Fisher-Porter aerosol compatibility bottle equipped with a magnetic stirrer as the reaction vessel. The reactor was charged with 7.6 grams (75 mmols) of lithium acetate dihydrate, 3.1 grams (10 mmols) of silver sulfate, 50 ml of acetic acid, 25 ml of acetic anhydride, and 10.7 grams (198.1 mmols) of butadiene charged from the vapor phase. The reactor was pressured to 30 psig with oxygen, placed in an oil bath and heated to 140° C. About 1 hour was required to bring the temperature of the bath up to the desired reaction temperature. The reaction was conducted for four hours during which the reactor was pressured intermittently to 120 psig with oxygen and then the reactor was allowed to cool overnight, and the reaction continued the following day for an additional 5 hour reaction period. Again during this period, the reactor was pressured intermittently to 120 psig with oxygen. At the end of the reaction period (total of 9 hours), the reactor was vented and the reaction mixture was filtered, and the filtrate then transferred to a distilling flask. The acetic acid was distilled away under 65 mm mercury pressure. There was also recovered 2.2 grams of unreacted butadiene in a cold trap. The distillation residue was mixed with ether, filtered through diatomaceous earth and the filtrate was washed with water, washed with sodium carbonate solution, then dried over magnesium sulfate and filtered. The ether was distilled away at atmospheric pressure. The reaction residue then weighed 14.8 grams and was analyzed by gas-liquid phase chromatography (GLC). This analysis showed that there had been produced 10.23 grams (59.5 mmols) of 1,2-diacetoxy-3-butene and 2.90 grams (16.9 mmols) of 1,4-diacetoxy-2-butene for a yield of diacetoxybutenes of 39 percent based on butadiene charged.

EXAMPLE II

Another run was conducted according to the instant invention employing the same apparatus as that used in Example I. In this run, the reactor was charged with 7.6 grams (75 mmols) of lithium acetate dihydrate, 6.7 grams (40 mmols) of silver acetate, 50 ml of acetic acid, 25 ml of acetic anhydride, and 11.5 grams (213 mmols) of butadiene charged from the vapor phase. The reactor was placed in an oil bath, pressured to 30 psig with oxygen and heated to 140° C. About 1 hour was required to bring the temperature of the oil bath up to the desired reaction temperature. During the reaction period of 6.8 hours, the reactor was intermittently pressured with oxygen to 120 psig. At the end of the reaction period, the reactor was vented and there was collected 0.5 grams of unreacted butadiene in a cold trap. The reaction mixture was filtered to recover 4.3 grams of white solid. The filtrate was transferred to a distilling flask and the acetic acid acid removed by distillation at 75 mm mercury pressure. The distillation residue was taken up in ether, filtered through diatomaceous earth, washed with water, washed with a sodium carbonate solution and then dried over magnesium sulfate and filtered. The ether was removed on a rotary evaporator. The residue remaining weighed 18.2 grams and was analyzed by gas-liquid phase chromatography (GLC). The analysis showed that there was obtained 11.15 grams (64.8 mmols) of 1,2-diacetoxy-3-butene and 3.42 grams (19.9 mmols) of 1,4-diacetoxy-2-butene for a yield of diacetoxybutenes of 40 percent based on the butadiene charged.

EXAMPLE III

A control run was conducted for the instant invention using the same apparatus as that employed in the previous two examples. In this run, the catalyst was silver acetate alone. The reactor was charged with 6.7 grams (40 mmols) of silver acetate, 50 ml of acetic acid, 25 ml of acetic anhydride, and 12.4 grams (229.6 mmols) of butadiene charged from the vapor phase. The reactor was placed in an oil bath, pressured to 30 psig with oxygen and heated to 140° C. About 0.5 hour was required to bring the temperature of the bath up to the desired reaction temperature. During the reaction period of 5 hours, the reactor was pressured intermittently with oxygen to 120 psig as in the previous two examples. At the end of the reaction period, the reactor was vented and the reaction mixture filtered to recover 6.3 grams of gray solid material. The filtrate was distilled through an 18 inch Vigreaux column to recover a fraction boiling at 50°-53° C at a pressure of 63 mm mercury. This fraction was analyzed by gas-liquid chromatography (GLC) and shown to be essentially pure acetic acid. The distillation residue, which weighed 19.2 grams was a thick black tar from which no diacetoxybutenes were recovered. The result of this run demonstrates that silver acetate alone was not suitable for the oxidation of butadiene in acetic acid to diacetoxybutenes, the product being rather an apparently polymeric material. On the other hand, Examples I and II demonstrate the operability of the catalyst system of this invention for oxidizing butadiene in acetic acid to produce diacetoxybutenes.

Reasonable variations and modifications, which will be apparent to those skilled in the art, can be made in this invention without departing from the spirit and scope thereof.

I claim:
1. A process for the production of unsaturated diesters which comprises reacting under reaction conditions a conjugated diolefin with a carboxylic acid in the presence of free oxygen and a catalytic amount of a catalyst system consisting of an alkali metal compound selected from the group consisting of the carboxylates and oxides thereof and a compound of a metal selected from the group consisting of gold and silver, said gold or silver compound being selected from the group consisting of the carboxylates, sulfates and oxides thereof wherein said conjugated diolefin is selected from the group consisting of acyclic conjugated diolefins having from 4 to 16 carbon atoms per molecule represented by the general formula

and cyclic conjugated diolefins having from 5 to 16 carbon atoms per molecule represented by the general formula

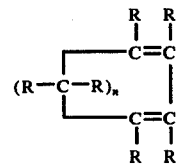

wherein, in each formula, each R is independently selected from the group consisting of hydrogen, halogen, cyano, —COOR', and alkyl, aryl and cycloalkyl radical groups and combinations thereof, of up to 12 carbon atoms per radical group, wherein R' is selected from the group consisting of hydrogen, alkyl of up to 10 carbon atoms and aryl of up to 10 carbon atoms and n is an integer having a value of 1 to 12; and wherein said carboxylic acid is selected from the group consisting of monocarboxylic acids having from 2 to 18 carbon atoms per molecule represented by the general formula

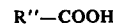

and dicarboxylic acids having from 2 to 18 carbon atoms per molecule represented by the general formula

wherein R" is selected from the group consisting of alkyl, cycloalkyl and aryl radical groups and halogen, cyano and —COOR' substituted derivatives thereof, wherein up to four of said halogen, cyano or —COOR' substituents can be present in said radical, wherein R' is selected from the group consisting of hydrogen, alkyl of up to 10 carbon atoms and aryl of up to 10 carbon atoms; and wherein R''' is selected from the group consisting of a valence bond and alkylene, cycloalkylene and arylene radical groups and halogen, cyano and —COOR' substituted derivatives thereof wherein up to four of said halogen, cyano or —COOR' substituents can be present in said radical, wherein R' is as defined above.

2. The process of claim 1 wherein said gold or silver compound is present in an amount ranging from about 0.1 to about 25 mole percent based on the conjugated diene and said alkali metal compound is present in an amount ranging from about 0.1 to about 2 molar based on said acid.

3. The process of claim 1 wherein said compound of gold or silver is supported on an inert support material.

4. The process of claim 1 wherein said reaction is carried out at a temperature in the range of 30° to about 200° C at an oxygen pressure in the range of 0.1 to 1000 psig above autogenous pressure at the temperature employed.

5. The process of claim 1 wherein there is additionally present a carboxylic acid anhydride corresponding to the carboxylic acid employed.

6. The process of claim 1 wherein said conjugated diolefin is 1,3-butadiene, said carboxylic acid is acetic acid and said catalyst system is silver sulfate and lithium acetate.

7. The process of claim 1 wherein said conjugated diolefin is 1,3-butadiene, said carboxylic acid is acetic acid and said catalyst system is silver acetate and lithium acetate.

8. The process of claim 1 wherein the molar ratio of said carboxylic acid to said conjugated diolefin is at least 2:1.

9. The process of claim 1 wherein said conjugated diolefin is an acyclic diolefin wherein R is hydrogen or alkyl.

10. The process of claim 1 wherein said carboxylic acid is a monocarboxylic acid.

* * * * *